United States Patent [19]

Long

[11] Patent Number: 5,169,314

[45] Date of Patent: Dec. 8, 1992

[54] CURET FOR PERIODONTAL TREATMENT

[76] Inventor: Barbara Long, 130 Saguenay Drive, Saskatoon, Saskatchewan, Canada, S7K 4G2

[21] Appl. No.: 484,054

[22] Filed: Feb. 23, 1990

[51] Int. Cl.$^5$ .............................................. A61C 17/00
[52] U.S. Cl. ...................... 433/143; 433/144
[58] Field of Search ................... 433/143, 144

[56] References Cited

U.S. PATENT DOCUMENTS

| | | | |
|---|---|---|---|
| 879,537 | 2/1908 | Gartrell | 433/143 |
| 1,220,933 | 3/1917 | Bates | 433/143 |
| 1,446,906 | 2/1923 | Kelsey | 433/143 |
| 1,844,913 | 2/1932 | Hallowell | 433/143 |
| 4,643,676 | 2/1987 | Jansheski | 433/143 |
| 4,759,713 | 7/1988 | Heiss et al. | 433/141 |

FOREIGN PATENT DOCUMENTS 0306267  3/1989  European Pat. Off. ............ 433/144
0382599 10/1907  France .................................. 433/143

OTHER PUBLICATIONS

Gracey Periodontal Finishing Curettes, Hu-Friedy Mfg. Co. Inc., 1985.

*Primary Examiner*—John J. Wilson
*Attorney, Agent, or Firm*—Hughes & Multer

[57] ABSTRACT

A dental curet adapted to remove calculus from the root surface of a person's teeth. The curet has a handle portion, a terminal shank, and a working end. A subgingival shank portion and the working end are arranged so that a working end lengthwise dimension from a rear surface of the lower part of the subgingival shank portion horizontally to the forward end of the toe portion is no greater than about 4 millimeters. The front toe portion of the working end extends in an upward and forward slant.

21 Claims, 7 Drawing Sheets

CURET FOR PERIODONTAL TREATMENT

The present invention relates to a curet for periodontal treatment, and more particularly to such a curet which is adapted to be operated in the sulcus, (i.e. the space between the person's gum and the tooth) for subgingival scaling and root-planing.

BACKGROUND ART

For a number of years, it is has been a standard part of dental hygiene to remove the calculus on tooth surfaces which can accumulate in the subgingival area. Quite commonly the dental hygienist will use a set of curets to accomplish this task.

One of the standards in the industry for many years has been the Gracey curets. This set of curets was designed by Dr. Clayton H. Gracey in the late 1930's. This comprises a set of curets designed for use in the specific areas of the mouth to make them particularly suitable for subgingival scaling and root planing of periodontal patients. Dr. Gracey's objectives were to design the curets to make it possible to reach into pockets where access is difficult in a manner to properly remove the calculus. The original instruments were designed to be used with a push stroke.

At a later time, there was a modified version to be used with pull strokes. These curets are characterized in that the blade is "offset" and only one cutting edge on each blade is used. Further, the blade is curved in two planes. These curets will be described in more detail later herein, with specific reference to the drawings.

A search of the U.S. Patent literature has disclosed two patents relating to these general types of dental instruments. These are as follows:

U.S. Pat. No. 1,220,933 (Bates) shows what is called a "dental scaler" where the working end of the instrument has a terminal shank portion having in its outer end a cutting blade C which is in the form of a quadrant of a circle, with a rounded cutting tip 1 and two cutting edges 2 and 3 on each side of the concave curved portion of the blade. The lower shank portion which leads into the cutting blade C is positioned at an angle to the lengthwise axis of the handle.

U.S. Pat. No. 4,643,676 (Jansheski) disclosed a dental tool to be used for personal oral hygiene. This comprises a handle having a hooked tip 12 which has a generally triangular cross section. The tipped portion is curved at about 45° to the lengthwise axis of the shank, and the radius of the curvature of the tip 14 is about 0.25 inches. There is a blunted-end tip 16.

SUMMARY OF THE INVENTION

The present invention is an improvement to a dental curet which is adapted to remove calculus from the root surface of a person's teeth, where the curet comprises:
 a. a handle portion adapted to be manually grasped;
 b. a terminal shank attached to and extending downwardly from said handle portion; and
 c. a working end having a rear heel portion attached to a lower end of the shank and a front toe portion, said working end having a blade edge portion and a lengthwise working axis extending laterally from the lower end of the shank to said toe portion.

In the improvement, the shank has a lower subgingival shank portion attached to the heel of the working end, and the lower subgingival shank portion has a lengthwise shank axis which has a substantial right angle component relative to the working axis, with the subgingival shank portion and the working end being arranged so that a working end lengthwise dimension from a rear surface of a lower part of said subgingival shank portion horizontally to the forward end of the toe portion is no greater than about 4 millimeters. Desirably this lengthwise dimension is no greater than about 3 millimeters, and more desirably between about 2 millimeters to 3 millimeters.

The rear heel portion of the working end has a center axis which curves through substantially a right angle curve with a heel radius of curvature no greater than about 3 millimeters. Desirably, this is no greater than about 2 millimeters, and more preferably between 1 to 2½ millimeters.

Further, in the preferred configuration, the front toe portion of the working end has an upwardly and forwardly slanting upper edge portion. In the preferred form, the upper end of said front toe portion is between about 0.1 to 0.3 millimeters above an upper edge of a portion of the working end located rearwardly of the front toe portion, and more desirably about 0.2 millimeters above the upper edge of the working end. Also, the upper edge portion of the front toe portion curves forwardly and upwardly with an end radius of curvature of no greater than about 3 millimeters, and more preferably no greater than about 2 millimeters.

In one of the embodiments of the present invention, the lower subgingival shank portion extends downwardly and forwardly at an angle relative to a longitudinal axis of the handle portion, and the working axis of the working end is at substantially a right angle to the subgingival shank portion and forms an angle less than a right angle with the longitudinal axis of the handle portion.

Other features will become apparent from the following detailed description.

DESCRIPTION OF THE PREFERRED EMBODIMENTS

As indicated previously, under "Background Art", the Gracey curets are commonly used for dental hygiene. A set of prior art Gracey curets can be made up of seven different instruments, with each instrument being specifically designed to operate effectively in a certain area of a person's teeth. The numerical designations of the Gracey instruments and the areas of the teeth for which these are designed to operate are as follows:

Gracey 1-2 (Anterior teeth)
Gracey 3-4 (Anterior teeth)
Gracey 5-6 (Anterior and bicuspid teeth)
Gracey 7-8 (Anterior and biscuspid teeth)
Gracey 9-10 (Posterior teeth—buccal and lingual surfaces)
Gracey 11-12 (Posterior teeth-mesial surfaces)
Gracey 13-14 (Posterior teeth-distal surfaces)

Figure 1A:
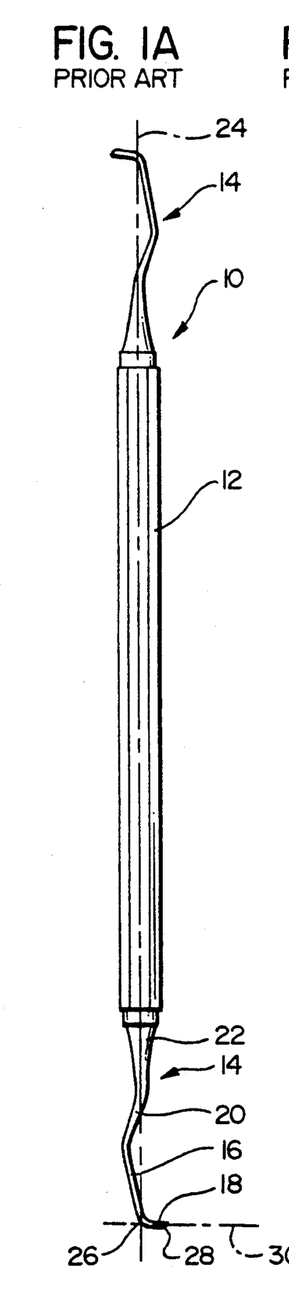
FIG. 1A is a side view of a prior art Gracey 5-6 curet adapted to be used with the anterior and bicuspid teeth.
Figure 1B:
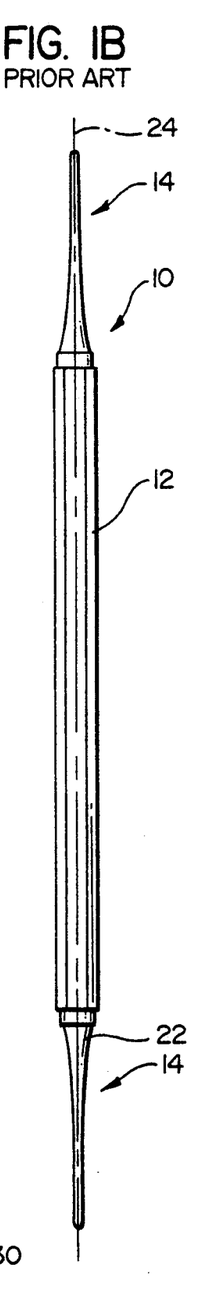
FIG. 1B is a rear view of the curet of FIG. 1.

In FIGS. 1A and 1B, there is shown a prior art Gracey 5-6 curet, this curet 10 comprising a handle 12 and upper and lower end portions 14. These end portions 14 are mirror images of one another so that one end portion 14 can operate on one side of the tooth, while the other end 14 can be used for corresponding tooth surface in the opposite side of the tooth. Each end portion 14 comprises a terminal shank 16 and a working end 18. Each terminal shank 16 joins to an intermediate shank portion 20 that in turn is connected to the adjacent end of the handle 12 by means of an upper shank portion 22.

The handle 12 has an elongate nearly cylindrical configuration, with the outside surface being flattened so that the cross sectional shape of the handle 12 is that of a regular hexagon, this enabling the curet to be grasped and manipulated more conveniently. The handle 12 has a longitudinal axis 24 which passes through the heel portion 26 of each working end 18. The terminal shank 16 of each end portion 14 slants upwardly and moderately rearwardly from the longitudinal axis 24, with the intermediate shank portion 20 extending upwardly and slanting moderately forwardly back to the location of the longitudinal axis 24.

For purposes of description, the longitudinal axis 24 of the curet 10 will be considered as being a vertical axis. The term "forward" will be used to denote a location proximate to a toe end 28 of the working portion 18 (or a direction extending from the heel end 26 to the toe end 28), while the term "rearward" or "rear" will be used to denote a location proximate to the heel 26 of the working end 18 (or a direction from the toe 28 to the heel 26). The term "lateral" or "sideways" will denote an axis or direction to one side or the other of a vertical plane defined by the vertical axis 24 and a forward to rear axis 30 extending through the heel 26 and the toe 28.

Figure 2A:
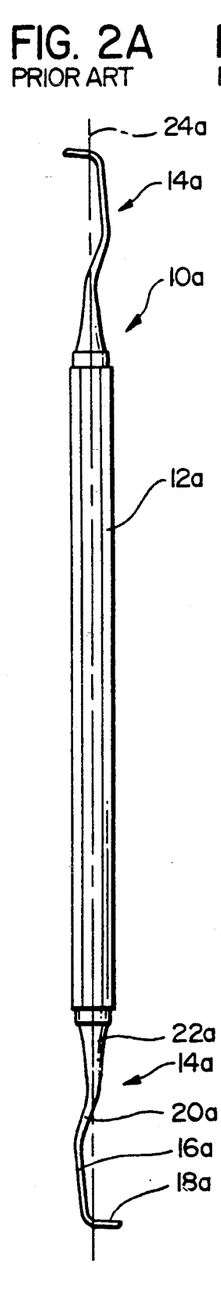
FIG. 2A and 2B are views similar to FIGS. 1A and 1B, respectively, showing a prior art 11-12 Gracey curet which is particularly adapted for use in connection with the mesial surfaces of the posterior teeth.
Figure 2B:
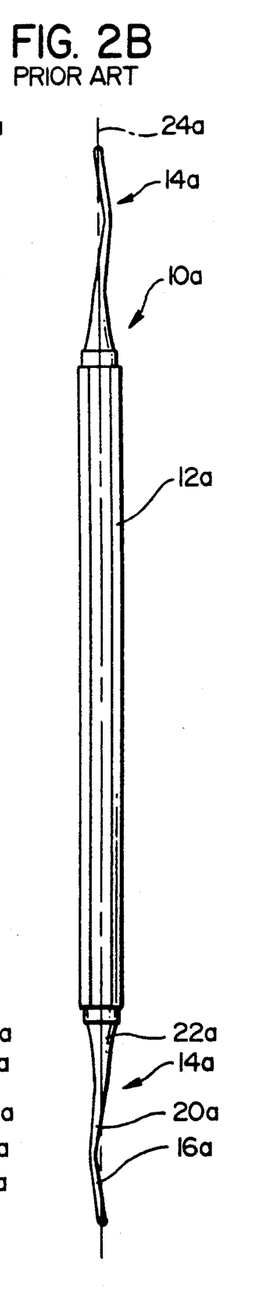

FIGS. 2A and 2B show the prior art Gracey 11-12 curet which is configured quite similar to the Gracey 5-6 curet of FIGS. 1A and 1B. Components of the curet of FIGS. 2A and 2B will be given numerical designations which are the same as corresponding components of the curet of FIGS. 1A and 1B, with an "a" suffix distinguishing those of the prior art Gracey curet of FIGS. 2A and 2B. The curet 10a of FIGS. 2A and 2B is substantially the same as those in FIGS. 1A and 1B, having a handle 12a and two end portions 14a, comprising terminal shanks 16a and end portions 18a. However, the lower shank portion 16a slants upwardly from a lower location adjacent to the vertical axis 24 to an upper location spaced a short distance laterally of the vertical axis 24. This permits the curet of FIGS. 2A and 2B to be used more effectively in the mesial surfaces of the posterior teeth.

Figure 3A:
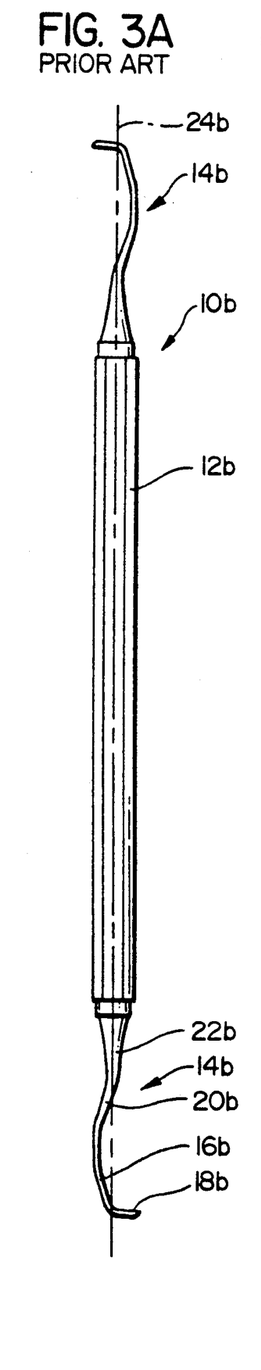
FIGS. 3A and 3B, respectively, are views similar to 1A and 1B and FIGS. 2A and 2B, showing the prior art Gracey 13-14 curet which is designed for use in connection with the distal surfaces of the posterior teeth.
Figure 3B:
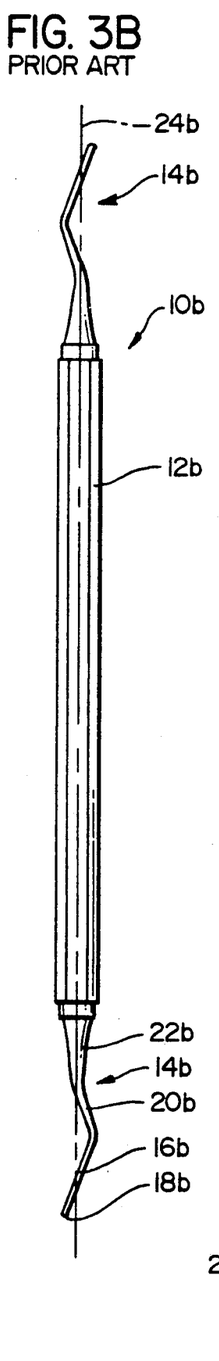

FIGS. 3A and 3B show the prior art Gracey 13-14 curet which is particularly configured to be used on the distal surfaces of the posterior teeth, and the corresponding components of the curet of FIGS. 3A and 3B will be given "b" suffixes to distinguish the curet of FIGS. 3A and 3B. It can be seen that the curet 10b is quite similar to those shown in FIGS. 1A and 1B and also FIGS. 2A and 2B, except at the upward and lateral slant of the lower shank portion 16B is at a greater angle from the vertical axis 4.

Figure 4A:
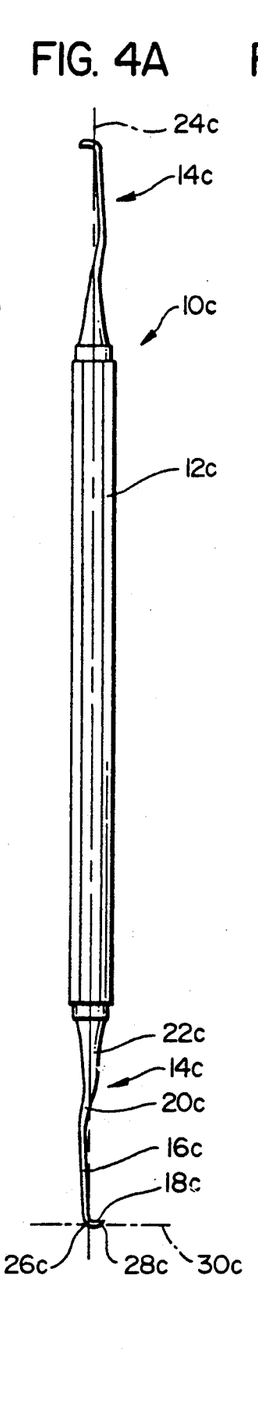
FIG. 4A is a side elevational view of a curet of a first embodiment of the present invention, which is designed for use in connection with the anterior and bicuspid teeth and which would correspond with the prior art Gracey 5-6 curet.
Figure 4B:
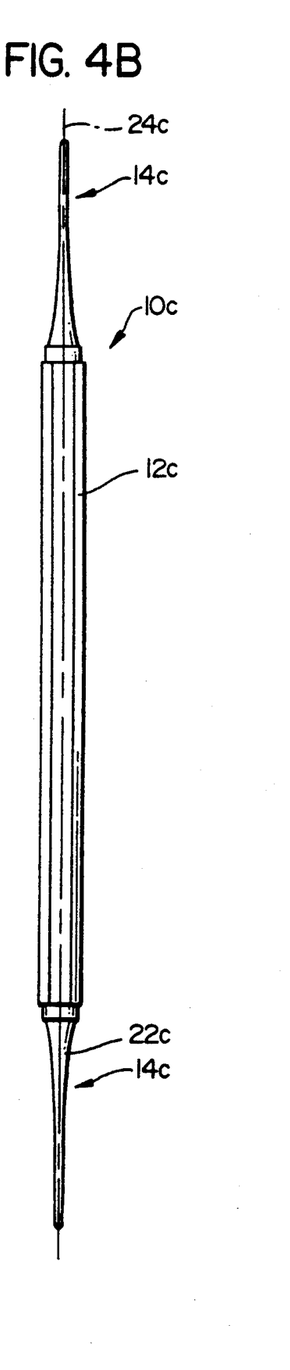
FIG. 4B is a rear elevational view of the curet of FIG. 4A.

FIGS. 4A and 4B show a curet 10c of a first embodiment of the present invention. Components of this first embodiment of the present invention will be given the same numerical designations as corresponding components of the Gracey curet of 1A and 1B, with a "c" suffix distinguishing those of the first embodiment of the present invention. Thus, the first embodiment 10c of the present invention comprises a handle 12c, two end portions 14c, a terminal shank 16c, a working end 18c, an intermediate shank portion 20c and a connecting shank portion 22c. Likewise, there is a vertical axis 24c, and the working end 18 has a heel portion 26c and a toe portion 28c, these being generally aligned on a forward to rear horizontal axis 30c. As with the prior art Gracey curet of FIGS. 1A and 1B, the curet of the first embodiment 10c shown in FIGS. 4A and 4B is particularly configured to be used in conjunction with the anterior and bicuspid teeth.

Figure 5A:
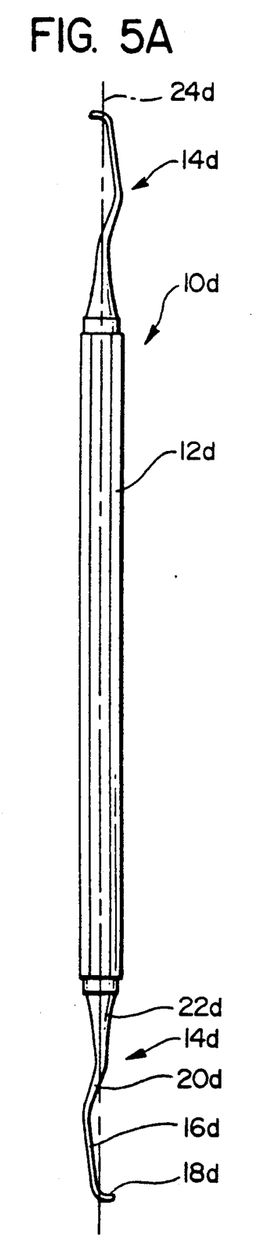
FIGS. 5A and 5B are similar to FIGS. 4A and 4B, respectively, showing a curet of a second embodiment of the present invention suitable for use in connection with the mesial surfaces of the posterior teeth, which would correspond to the prior art Gracey 11-12 curet.
Figure 5B:
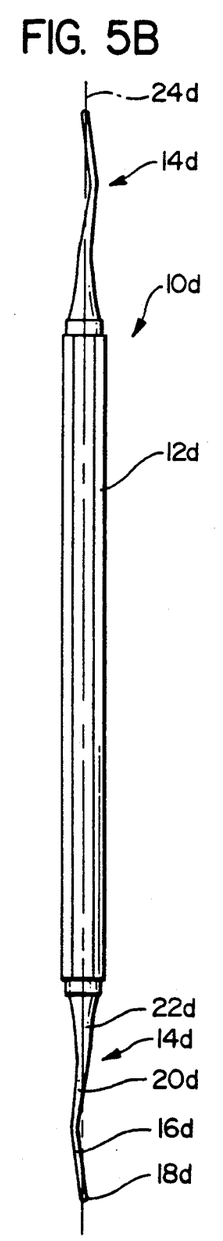

FIGS. 5A and 5B show a second embodiment of the present invention, and components of this second embodiment will be given "d" suffixes to numerical designations which will correspond to similar components of the first embodiment of FIGS. 4A and 4B. The second embodiment of the present invention shown in FIGS. 5A and 5B is similar to the prior art Gracey curet shown in FIGS. 2A and 2B in that both of these are particularly designed to be used in conjunction with the mesial surfaces of the posterior teeth.

Figure 6A:
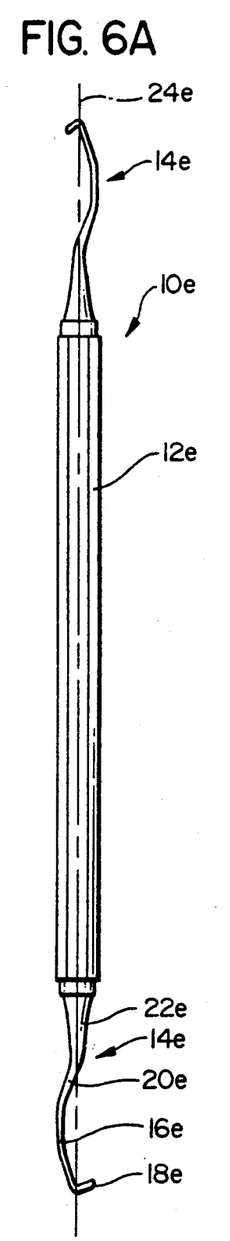
FIGS. 6A and 6B correspond FIGS. 4A and 4B and also FIGS. 5A and 5B, and show a curet of a third embodiment of the present invention suitable for cleaning the distal surfaces of the posterior teeth, this corresponding to the prior art Gracey 13-14 curet.
Figure 6B:
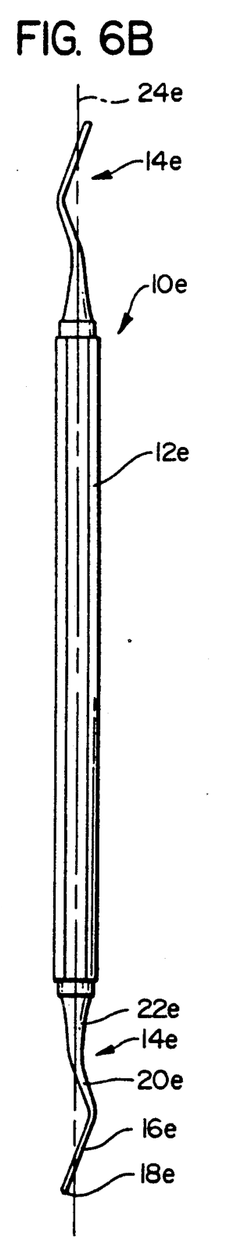

FIGS. 6A and 6B show a third embodiment of the present invention, and components of this third embodiment will be given numerical designations that correspond to similar components of the first and second embodiments of the present invention, with suffix "e" distinguishing those components of the third embodiment. This third embodiment of FIGS. 6A and 6B is similar to the prior art Gracey 13-14 curet, in that it is particularly adapted to be used in conjunction with the distal surfaces of the posterior teeth.

Figure 7:
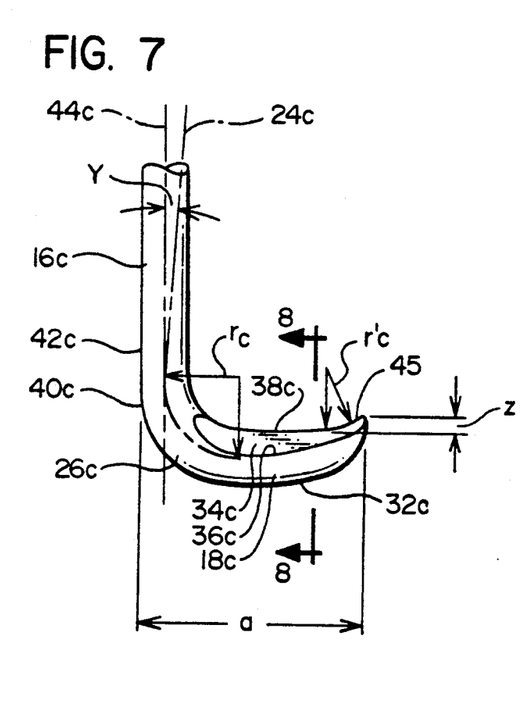
FIG. 7 is a side elevational view of the lower portion of the curet of the first embodiment shown in FIG. 4A, but drawn to an enlarged scale.

To describe further the first embodiment of the present invention shown in FIGS. 4A and 4B, reference is now made to FIG. 7, which shows only the terminal shank 16c and the working end 18c of the first embodiment 10c of the present invention.

Figure 8:
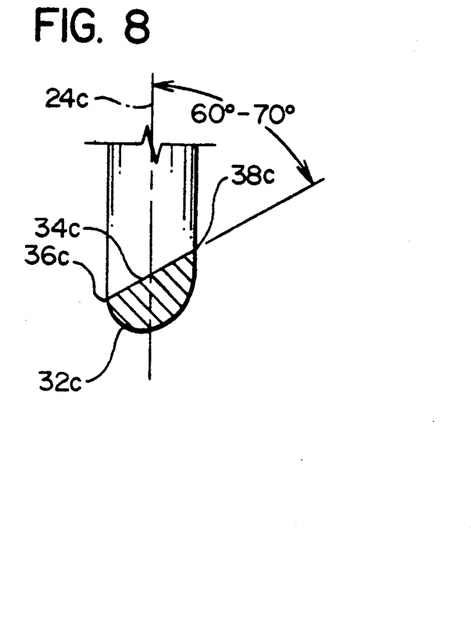
FIG. 8 is a sectional view taken along line 8—8 of FIG. 7 showing the working end portion of the curet of FIG. 7.

The terminal shank 16c has in horizontal cross section a cylindrical configuration, and at the lower end thereof, it curves in a downward and forward direction through approximately a 90° curve at the heel portion 26c of the working end 18c. As can be seen in FIG. 8, the lower surface 32c of the working end 18c has in transverse cross section a semi-circular configuration, while the upper surface 34c has a planar configuration which slants at an angle of 60° to 70° (as seen in a vertical transverse plane perpendicular to the forward to rear axis 30c) to the vertical axis 24c. The upper surface 34c meets the lower surface 32c at a lower working edge portion 36c, and the surface 32c meets the surface 34c at an opposite upper edge portion 38c. In the normal mode of operation of the curet 10c, the edge 36c engages the root surface in the subgingival area of the tooth to remove the calculus.

It should be noted that this arrangement of a slanted upper surface at 34c also exists with the prior art Gracey curet of FIGS. 1A-1B through FIGS. 3A-B.

Figure 9:
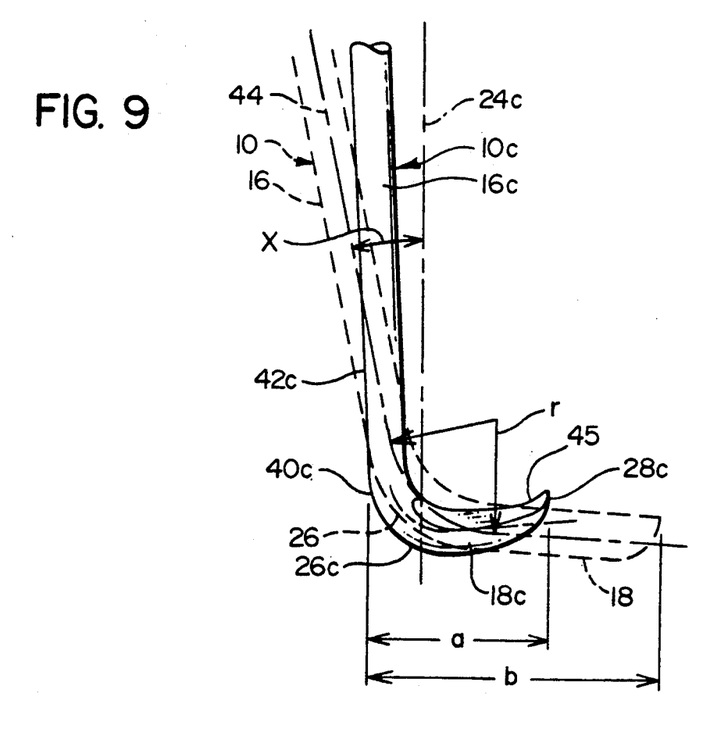
FIG. 9 is a view similar to FIG. 7, showing in full lines the curet of the first embodiment of the present invention, and in broken lines the prior art Gracey 5-6 curet, this being done to show the distinctive features of the present invention.

To demonstrate the differences between the first embodiment 10c of the present invention and the prior art Gracey 5-6 curet 10, reference is now made to FIG. 9, which shows the curet 10c of the present invention in full lines, and the prior art Gracey curet 10 in broken lines. It will be noted that the heel portion 26c has, in side elevational view, a curved configuration of approximately 90°. The upper rear end portion 40c of the curved heel portion 26c joins to a rear surface 42c of the lower shank 16c. The shank 16c is aligned nearly vertically with the vertical axis 24c.

A significant feature of the present invention is that the length of the working end portion 18, as measured from the rear location 40c of the heel portion 26c to the forward-most end of the toe 28c (indicated at "a" in FIG. 9) is desirably between about 2 to 3 millimeters, and in no event is greater than about 4 millimeters. The total length of the working end 18 of the corresponding prior art Gracey curet 10 is, as shown at "b" in FIG. 9) approximately 6 millimeters. Also, it will be noted that a radius of curvature $r_c$ of a center axis of the curved heel portion 26c (an axis extending along the center line of the heel portion 26c) is about 2 millimeters, while the corresponding center axis of the heel portion 26 of the prior art Gracey 5-6 curet 10 (indicated at "r" is about 4 millimeter. Further, the angle of the center axis 44 of the terminal shank 16 of the prior art Gracey 5-6 curet 10 makes an angle (indicated at "x") in FIG. 9 with the vertical axis of about 8°. The center axis 44c of the first embodiment (indicated at "y" in FIG. 7) makes with the vertical axis 24c an angle of no greater than about 1 to 3°, and more desirably no greater than about 1°. The toe portion 28c curves upwardly from the edge 38c to a height of about 0.2 millimeters above the edge 38c (indicated at "Z"). The radius of curvature of the curved portion 45 immediately rearwardly of the toe 28c (indicated at r'c) is about 2 millimeters.

Figure 10:
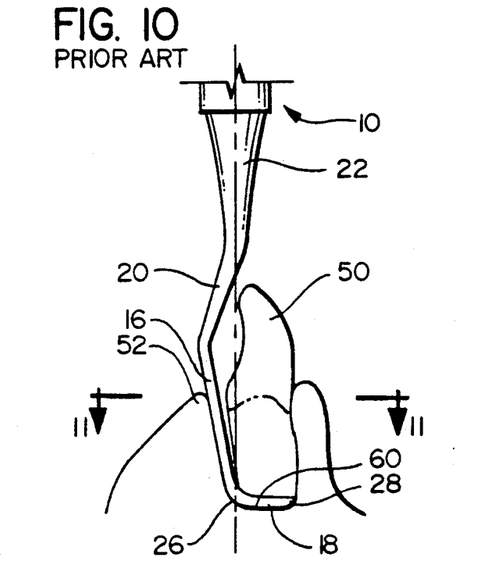
FIG. 10 is an elevational view showing the prior art Gracey 5-6 of FIGS. 1A and 1B in one operating position in the subgingival area in the interproximal location.
Figure 11:
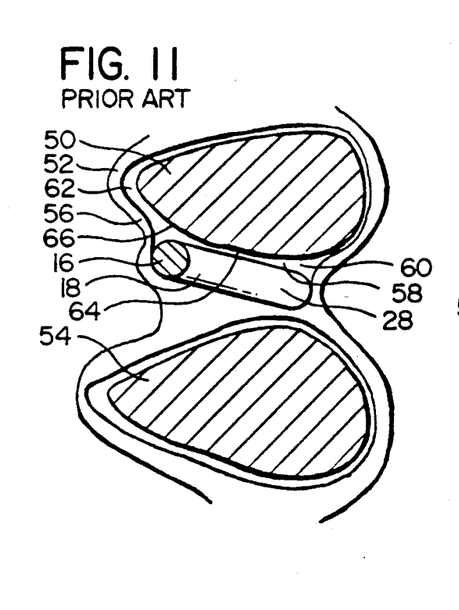
FIG. 11 is a sectional view taken along a horizontal plane at line 11—11 of FIG. 10.

To demonstrate one of the significant advantages of the present invention, reference is first made to FIGS. 10 and 11 which illustrates one manner in which the prior art Gracey 5-6 curet can be used. There is shown a person's tooth 50 with the gum 52 surrounding the lower portion of the tooth 50. In FIG. 11, there is shown in horizontal cross section the tooth 50 and also a second tooth 54. The gum 52 has a labial portion 56 and an interproximal portion 58 (that portion between the two teeth 50 and 54). The subgingival area 60 (also called the sulcus) is the area between the gum 52 and the tooth 50 or 54. In FIG. 10, the working end 18 is shown as positioned horizontally in the sulcus 60. It can be seen that the heel 26 of the working end 18 presses the inside surface of a labial portion 56 of the gum 52 outwardly, while the toe 28 presses against an interproximal portion 58 of the gum 52. The reason for this is that the labial surface 62 of the tooth 50 at the location of the gum 52 joins the interproximal surface 64 of the tooth 50 along a curved portion 66. As the working end 18 is moved around this curved portion 66, there tends to be a stretching of the gum 52 at locations adjacent to the heel 26 and the toe 28.

While the stretching of the gum (as illustrated in FIG. 11) may not cause a great deal of discomfort for a person with healthy gums, and little calculus where the depth of the subgingival area is no greater than one to two millimeters or possibly as great as three millimeters, in those instances where the gum is diseased or there is a large deposit of calculus and it is necessary for the working end 18 to extend further downwardly into the subgingival area 60, the subsequent stretching of the gum 52 can cause greater discomfort.

Figure 12:
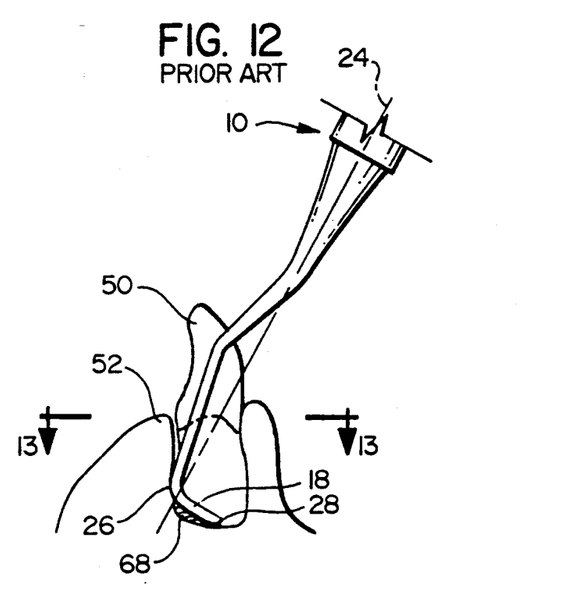
FIG. 12 is a view similar to FIG. 10, but showing the prior art Gracey 5-6 curet in an alternative operating position at the interproximal area.
Figure 13:
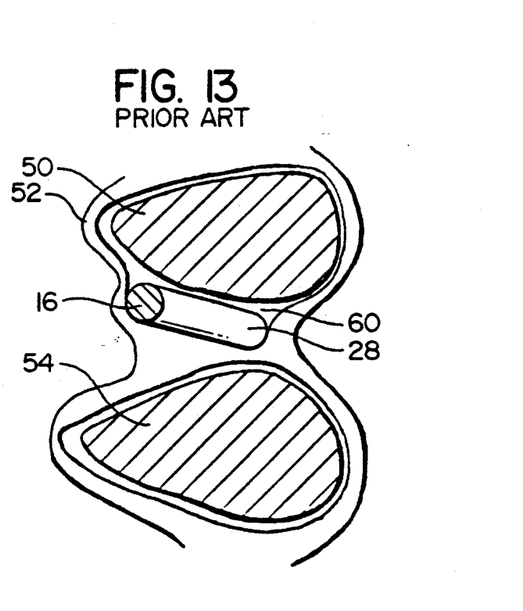
FIG. 13 is a horizontal sectional view taken at line 13—13 of FIG. 12.

Accordingly, a skilled operator will sometimes change the angle at which the curet 10 is operated so that the toe end 28 of the working end 18 can extend further downwardly into the sulcus 60. This is illustrated in FIG. 12, where it can be seen that the vertical axis 24 of the curet 10 is tilted from the vertical so that the working end portion 18 slants downwardly in a forward direction toward the toe 28. In this position, the heel 26 does not extend into the sulcus to any great extent, and the stretching of the gum 52 is alleviated. However, it can be appreciated that if the gum 52 is diseased to any extent so that it is necessary for the working end 18 to penetrate further downwardly into the subgingival area, it is necessary for the heel 26 to extend into the subgingival area, since there are practical limits as to how much the curet 10 can be tilted because of the location of the person's teeth relative to the structure of the person's face.

Further, it should be noted that when the working end 18 is tilted, there is an area near the middle and rear portion of the working end 18 (indicated in the shaded area at 68) where the working end 18 has difficulty in reaching.

Figure 14:
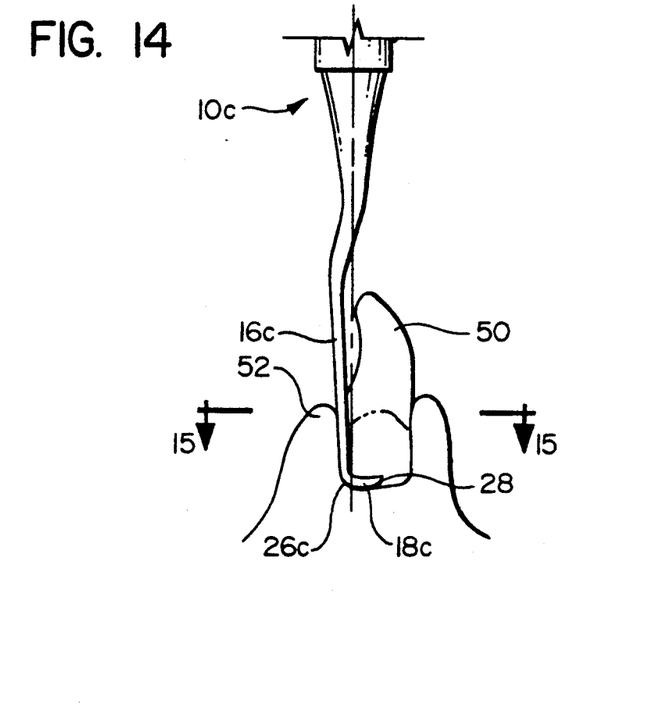
FIG. 14 is a view similar to FIG. 10, but showing the curet of the first embodiment of the present invention operating in the subgingival, interproximal area.
Figure 15:
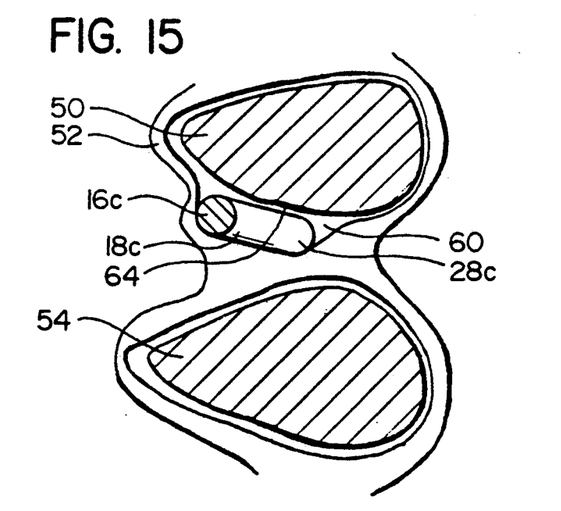
FIG. 15 is a sectional view taken along line 15—15 of FIG. 14.

To demonstrate the manner in which the curet of the first embodiment 10c of the present invention accomplishes the periodontal treatment as indicated in FIGS. 10 through 13, reference is now made to FIG. 14 and 15, where the curet 10c of the first embodiment of the present invention is shown performing the same periodontal operation as illustrated in FIGS. 10 through 13. It can be seen in FIGS. 14 and 15 that the working end 18c can be positioned in the sulcus 60 in a manner that the heel portion 26c and the toe portion 28c remain reasonably close to the interproximal area between the teeth 50 and 54. It has been found that the shortened length dimension (illustrated at "a" in FIGS. 8 and 9) of the working end 18c of the present invention greatly enhances the ability of the curet 10c to be positioned in the sulcus 60 without any significant discomfort, particularly where the gum 52 is diseased to some extent so that it is necessary to penetrate to a greater depth in the sulcus 60. Further, since the radius of curvature (indicated at "$r_c$" in FIG. 7) is relatively small, the working edge 36c (see FIGS. 7 and 8) can still have adequate length to enable effective operation of the curet 10c. Also, since the alignment of the terminal shank portion 16c is very closely aligned to the vertical axis 24, greater penetration into the sulcus 60 can be accomplished without distending the gum 52 unnecessarily. Thus, the working end 18c of the first embodiment of the present invention can be aligned nearly horizontal in various locations around the base of the tooth 50, thus having the effect of operating in the area 68 (see FIG. 12) which was difficult to reach with the prior art curet 10.

Figure 16A:
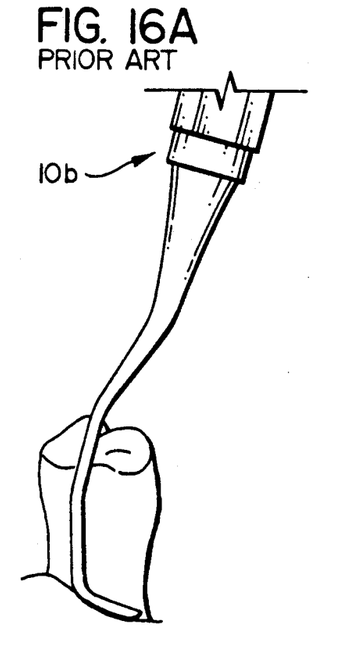
FIG. 16A is a side elevational view of a prior art Gracey 13-14 curet positioned in the interproximal subgingival area to work on the distal surface of a posterior tooth.
Figure 16B:
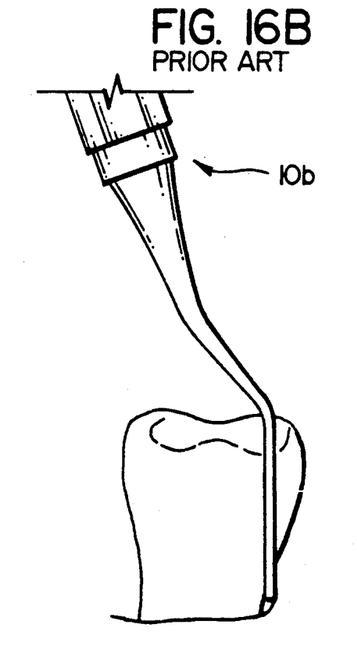
FIG. 16B is a rear elevational view of the prior art Gracey 13-14 curet of FIG. 16A.
Figure 17A:
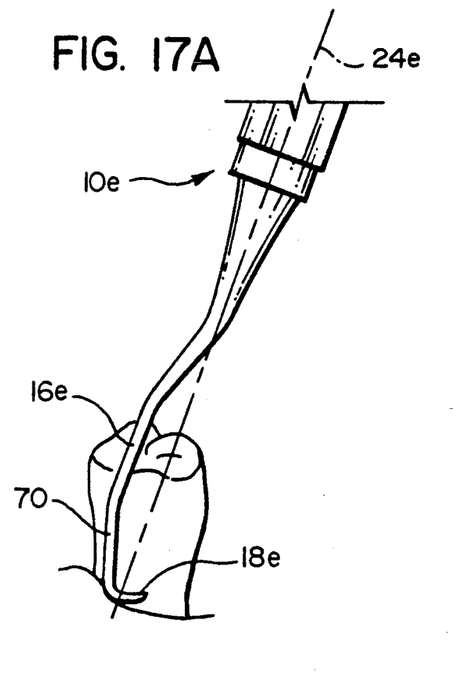
FIG. 17A is a view similar to FIG. 16A, but showing the curet of the present invention positioned in the interproximal area of a posterior tooth to engage the distal surface.
Figure 17B:
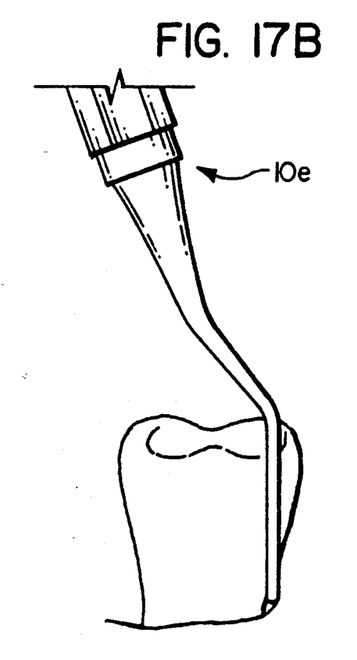
FIG. 17B is a rear elevational view of the curet of the present invention as shown in FIG. 17A.

To illustrate the manner in which the curet of the third embodiment of the present invention (shown in FIGS. 6A and 6B) is used in comparison with a corresponding Gracey curet (as shown in FIGS. 3A and 3B) reference is now made to FIGS. 17A and 17B (which illustrates the curet of the third embodiment of FIGS. 6A and 6B in operation) and also FIG. 16A and 16B (which shows the prior art Gracey curet of FIGS. 3A and 3B in operation). It can be seen that the working end 18e of the third embodiment of the present invention is able to fit into the subgingival area and remain closer to the surface of the tooth at which the working end 18e is operating. Further, the working end 18e of the third embodiment makes an angle of close to 90° with the lower shank portion 70 which is at an angle of between 10° to 20° (desirably about 15°) with the vertical axis 24e. Thus, when the curet 10e is positioned as shown in FIGS. 17A and 17B, the working end 18e is properly positioned.

It is to be understood that various modifications could be made to the present invention without departing from the basic teachings thereof.

What is claimed:

1. In a dental curet adapted to remove calculus from the root surface of a person's teeth, where said curet comprises:
    a. a handle portion adapted to be manually grasped;
    b. a terminal shank portion attached to and extending downwardly from said handle portion; and
    c. a working end having a rear heel portion attached to a lower end of the shank and a front toe portion, said working end having a blade edge portion and a lengthwise working axis extending laterally from the lower end of the shank to said toe portion;

an improvement comprising said shank having a lower subgingival shank portion that attaches to the heel of the working end, with said lower subgingival shank portion having a lengthwise shank axis which has a substantial right angle alignment component relative to said working axis, said subgingival shank portion and said working end being arranged so that a working end lengthwise dimension from a rear surface of a lower part of said subgingival shank portion horizontally to the forward end of the toe portion is no greater than about 4 millimeters.

2. The improvement as recited in claim 1, wherein said lengthwise dimension of the working end is no greater than about 3 millimeters.

3. The improvement as recited in claim 1, wherein said lengthwise dimension of the working end is between about 2 millimeters to 3 millimeters.

4. The improvement as recited in claim 1, wherein the rear heel portion of the working end has a center axis which curves through substantially a right angle curve with a heel radius of curvature no greater than about 3 millimeters.

5. The improvement as recited in claim 5, wherein said radius of curvature is no greater than about 2 millimeters.

6. The improvement as recited in claim 5, wherein said radius of curvature is between about 1 to 2.5 millimeters.

7. The improvement as recited in claim 1, wherein the front toe portion of the working end has an upper edge portion which slants upwardly and forwardly relative to the lengthwise working axis of the working end.

8. The improvement as recited in claim 7, wherein an upper end of said front toe portion is at about 0.1 to 0.3 millimeters above an upper edge of a portion of said working end located rearwardly of said front toe portion.

9. The improvement as recited in claim 8, wherein said front toe portion is about 2 millimeters above said upper edge of said working end.

10. The improvement as recited in claim 7, wherein said upper edge portion of said front toe portion curves forwardly and upwardly with an end radius of curvature of no greater than about 3 millimeters.

11. The improvement as recited in claim 10, wherein said radius of curvature is no greater than about 2 millimeters.

12. The improvement as recited in claim 1, wherein said lower subgingival shank portion extends downwardly and forwardly at an angle relative to a longitudinal axis of said handle portion, and said working axis of the working end is at substantially a right angle to said subgingival shank portion and forms an angle less than a right angle with the longitudinal axis of the handle portion.

13. The improvement as recited in claim 1, wherein:
    a. the rear heel portion of the working end has a center axis which curves through substantially a right angle curve with a heel radius of curvature no greater than about 3 millimeters;
    b. the front toe portion of the working end has an upper edge portion which slants upwardly and forwardly relative to lengthwise working axis of the working end.

14. The improvement as recited in claim 13, wherein said upper edge of said front toe portion curves forwardly and upwardly with an end radius of curvature of no greater than about 3 millimeters.

15. The improvement as recited in claim 14, wherein
   a. said lengthwise dimension of the working end is between about 2 millimeters to 3 millimeters.
   b. said radius of curvature is no greater than about 2 millimeters.
   c. an upper end of said front toe portion is, relative to the lengthwise working axis of said working end, at about 0.1 to 0.3 millimeters above an upper edge of a portion of said working end located rearwardly of said front toe portion.

16. In a dental curet adapted to remove calculus from the root surface of a person's teeth, where said curet comprises:
   a. a handle portion adapted to be manually grasped;
   b. a terminal shank attached to and extending downwardly from said handle portion: and
   c. a working end having a rear heel portion attached to a lower end of the shank and a front toe portion, said working end having a blade edge portion and a lengthwise working axis extending laterally from the lower end of the shank to said toe portion;
an improvement comprising said shank having a lower subgingival shank portion that attaches to the heel portion of the working end, with said lower subgingival shank portion having a lengthwise shank axis which has a substantial right angle alignment component relative to said working axis, the front toe portion having an an edge portion which slants upwardly and forwardly and which makes an angle with a longitudinal axis of said handle portion of less than a right angle.

17. The improvement as recited in claim 16, wherein an upper end of said front toe portion is at about 0.1 to 0.3 millimeters above an upper edge of a portion of said working end located rearwardly of said front toe portion.

18. The improvement as recited in claim 17, wherein said front toe portion is about 2 millimeters above said upper edge of said working end.

19. The improvement as recited in claim 17, wherein the rear heel portion of the working end has a center axis which curves through substantially a right angle curve with a heel radius of curvature no greater than about 3 millimeters.

20. The improvement as recited in claim 19, wherein said radius of curvature is no greater than about 2 millimeters.

21. The improvement as recited in claim 16, wherein said upper edge of said front toe portion curves forwardly and upwardly with an end radius of curvature of no greater than about 3 millimeters.

* * * * *